(12) United States Patent
Lu et al.

(10) Patent No.: US 11,434,464 B2
(45) Date of Patent: Sep. 6, 2022

(54) PERFUSION BIOREACTOR WITH FILTRATION SYSTEMS

(71) Applicant: Genzyme Corporation, Cambridge, MA (US)

(72) Inventors: Jiuyi Lu, Topsfield, MA (US); Jason Walther, Holliston, MA (US); Jonathan Wang, Brighton, MA (US); Kevin Victor Chen, Marlborough, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 17/524,269

(22) Filed: Nov. 11, 2021

(65) Prior Publication Data
US 2022/0073861 A1 Mar. 10, 2022

Related U.S. Application Data

(63) Continuation of application No. 16/403,161, filed on May 3, 2019.
(Continued)

(51) Int. Cl.
*B01D 15/18* (2006.01)
*B01D 61/18* (2006.01)
(Continued)

(52) U.S. Cl.
CPC ......... *C12M 41/48* (2013.01); *B01D 15/1807* (2013.01); *B01D 61/18* (2013.01);
(Continued)

(58) Field of Classification Search
CPC ...... C12M 41/48; C12M 29/04; C12M 29/10; C12M 41/40; C12M 43/00; C12M 29/16;
(Continued)

(56) References Cited

U.S. PATENT DOCUMENTS 5,470,464 A * 11/1995 Priegnitz ............ B01D 15/1842
210/198.2
6,544,424 B1 * 4/2003 Shevitz .................. C12M 47/10
210/650
(Continued)

FOREIGN PATENT DOCUMENTS

WO 2015039115 3/2015
WO 2018015386 1/2018

*Primary Examiner* — Joseph W Drodge
(74) *Attorney, Agent, or Firm* — Mcdonnell Boehnen Hulbert & Berghoff LLP

(57) ABSTRACT

The disclosure provides a filtration system for a cell culture apparatus and a method of cell culture. The filtration system comprises a bioreactor vessel and two or more alternating tangential flow (ATF) filters connected in parallel. A failure in either filter is detected by an in-line sensor, and an automated response system functions to sequester the malfunctioning filter by stopping the flow of liquid media through the filter. Media flow through the remaining operable filters can be increased so that the rate of perfusion through the bioreactor remains relatively unchanged. Such a system may prevent issues that arise from ATF filter failures in conventional perfusion bioreactors, thereby improving the long-term viability of cell cultures.

15 Claims, 3 Drawing Sheets

Related U.S. Application Data

(60) Provisional application No. 62/667,319, filed on May 4, 2018.

(51) Int. Cl.
  B01D 61/22 (2006.01)
  C12M 1/36 (2006.01)
  C12M 1/00 (2006.01)
  C12M 1/34 (2006.01)

(52) U.S. Cl.
  CPC .............. B01D 61/22 (2013.01); C12M 29/04 (2013.01); C12M 29/10 (2013.01); C12M 41/40 (2013.01); *B01D 2311/2626* (2013.01); *B01D 2311/2688* (2013.01); *B01D 2313/243* (2013.01); *B01D 2315/10* (2013.01); *B01D 2317/04* (2013.01); *B01D 2317/06* (2013.01)

(58) Field of Classification Search
  CPC ...... C12M 33/14; C12M 47/04; C12M 47/12; B01D 15/1807; B01D 61/18; B01D 61/22; B01D 2311/2626; B01D 2311/2688; B01D 15/125; B01D 61/14; B01D 61/142; B01D 61/145; B01D 61/147; B01D 61/20; B01D 63/04; B01D 63/046; B01D 2311/06; B01D 2311/08; B01D 2313/10; B01D 2313/243; B01D 2315/10; B01D 2317/04; B01D 2317/06; B01D 2319/04; A61M 1/34
  See application file for complete search history.

(56) References Cited

U.S. PATENT DOCUMENTS

| | | | |
|---|---|---|---|
| 2005/0023194 A1* | 2/2005 | Petersen | B01D 63/08 210/85 |
| 2006/0051347 A1* | 3/2006 | Winter | C07K 16/065 424/133.1 |
| 2008/0269468 A1* | 10/2008 | Vogel | C07K 14/755 530/414 |
| 2013/0270165 A1* | 10/2013 | Shevitz | C12M 29/04 210/205 |
| 2013/0319944 A1* | 12/2013 | Pralong | B01D 61/22 210/650 |
| 2014/0093952 A1 | 4/2014 | Serway | |
| 2014/0227769 A1* | 8/2014 | Strobbe | C12N 5/0607 435/287.1 |
| 2014/0273206 A1* | 9/2014 | Jin | C12M 33/14 435/350 |
| 2015/0133636 A1* | 5/2015 | Xenopoulos | C07K 1/36 530/387.1 |
| 2015/0158907 A1* | 6/2015 | Zhou | C07K 14/52 435/183 |
| 2016/0144320 A1* | 5/2016 | Nishio | B01D 61/147 435/297.1 |
| 2017/0026825 A1* | 1/2017 | Yang | H04W 8/183 |
| 2017/0080390 A1* | 3/2017 | Tomescu | B01D 61/145 |
| 2017/0128905 A1* | 5/2017 | Pighin | B01D 61/22 |
| 2017/0157566 A1* | 6/2017 | Gefroh | B01D 61/142 |
| 2017/0173537 A1* | 6/2017 | Gagnon | C12M 47/10 |
| 2017/0260498 A1* | 9/2017 | Mundt | A61L 2/0017 |
| 2018/0051054 A1* | 2/2018 | Vetter | B01D 15/1864 |
| 2019/0338238 A1* | 11/2019 | Lu | B01D 61/18 |
| 2020/0139303 A1* | 5/2020 | Dupont | B01D 63/10 |

* cited by examiner

PERFUSION BIOREACTOR WITH FILTRATION SYSTEMS

CROSS REFERENCE TO RELATED APPLICATIONS

This application is a continuation of U.S. application Ser. No. 16/403,161, filed May 3, 2019, which claims the benefit of U.S. Provisional Application No. 62/667,319, filed May 4, 2018, the disclosures of each of which are explicitly incorporated by reference herein.

TECHNICAL FIELD

The disclosure relates generally to a perfusion cell culture apparatus and a method of cell culture.

BACKGROUND

In vitro cell culture is the complex process by which cells are grown under controlled conditions outside of their natural environment. Culture conditions may vary for each cell type, and must be precisely controlled to ensure the correct cell phenotype and/or expression of a desired product.

Bioreactors provide a controlled environment to grow and maintain cells according to their temperature, pH, nutrition, gas, and other needs. In order to culture cells for an extended period of time, fresh media must be continuously supplied to the cells, and spent media must be removed at approximately the same rate. To extend the productive duration of cell culture within a bioreactor, perfusion bioreactors have been developed which continuously perfuse cells with fresh media, and harvest a desired product while retaining cells in the bioreactor. Such bioreactors have allowed cells to be grown at higher cell concentrations and maintained for extended periods of time relative to bioreactors without active perfusion systems.

FIG. 1 shows a schematic of a typical state-of-the-art perfusion bioreactor 100, as is known by those familiar with the field. The perfusion bioreactor includes a bioreactor vessel 110, an alternating tangential flow (ATF) filter 120, a harvest pump 130, and a continuous capture operation 160. The perfusion bioreactor 100 can be operated by (i) attaching an ATF filter device 120 to the bioreactor vessel 110; (ii) filling the bioreactor vessel 110 with fresh media; (iii) inoculating the bioreactor vessel 110 with cells; and (iv) perfusing fresh media into the bioreactor vessel 110 and removing spent media via the harvest pump 130 in series with the ATF filter 120.

Under these conditions, cells may be cultured and maintained for an extended period of time. The continually added media gives the cells the nutrients they require to grow, and the removed spent media allows cellular wastes and byproducts to be removed from the system to prevent them from reaching harmful levels. The ATF filter allows spent media to be removed from the bioreactor while retaining the cells within the bioreactor. Other cell culture parameters are typically also controlled to improve performance and robustness, including temperature, dissolved oxygen, pH, $pCO_2$, and cell density.

As shown in FIG. 1, the perfusion bioreactor 100 can be integrated with a continuously operating capture operation 160. In this scenario, the spent media being removed from the bioreactor vessel 110 contains the product of interest and is continuously fed to the continuous capture operation 160 where it is processed and purified in some manner.

A standard perfusion bioreactor, such as the bioreactor shown in FIG. 1, may be intended to run for long durations of time (30-60 days, if not longer). However, equipment robustness can prove to be limiting. In particular, the ATF filter can fail, leading to process disruption or perturbation. In some cases, the ATF filter can fail catastrophically such that it allows cells to pass through the filter and into the harvest. Such an incident can have a variety of negative impacts. First, because cells are no longer retained in the bioreactor by the ATF, they can quickly flow out of the bioreactor and the cell density and productivity of the bioreactor may decrease. Second, in a system integrated with a downstream continuous purification step, cells may flow directly into that operation, harming the purification system. In one example, cells could pass onto the columns on a periodic continuous counter-chromatography (PCC) skid, leading to clogging, pressurization, and increased introduction of impurities. In such a situation, the problem must be quickly identified and the ATF must be quickly replaced to preserve the bioreactor. Independently, the downstream operation would likely need to be shut down and cleaned, and single-use parts may need to be replaced. The entire response could lead to days of lost production and, at worst, lead to an entire run shutdown.

SUMMARY

An apparatus and method for cell cultivation that overcomes one or more of the disadvantages known in the art is provided. It has been found that it is possible to prepare a filtration system for a perfusion cell culture apparatus that automatically detects and responds to an ATF filter malfunction, without the need to shut down the cell culture operation.

In a first embodiment of the disclosure, a perfusion cell culture apparatus is provided. The apparatus includes a bioreactor vessel, a first filtration assembly, a second filtration assembly, and a controller. The bioreactor vessel is configured to receive liquid media. The first filtration assembly is in fluid communication with the bioreactor vessel and includes a first filtration system, a first harvest pump, and a sensor. The first harvest pump is connected in series with the first filtration system and is configured to pump the liquid media from the bioreactor vessel through the first filtration system. The sensor is configured to interact with the liquid media inside the first filtration assembly. The second filtration assembly is also in fluid communication with the bioreactor vessel and is configured to operate in parallel with the first filtration assembly. The second filtration assembly includes a second filtration system and a second harvest pump. The second harvest pump is connected in series with the second filtration system and is configured to pump the liquid media from the bioreactor vessel through the second filtration system. The controller executes operations. The operations include receiving, from the sensor, information indicative of an operational state of the first filtration system. The operations further include determining, based on at least the received information, whether the first filtration system is in an operable state. The operations also include, responsive to a determination that the first filtration system is not in an operable state, causing the first harvest pump to stop pumping liquid media through the first filtration system.

In a second embodiment of the disclosure, a perfusion cell culture apparatus is provided. The apparatus includes a bioreactor vessel, a filtration assembly, and a controller. The bioreactor vessel is configured to receive liquid media. The filtration assembly is in fluid communication with the bioreactor vessel and includes a filtration system, a harvest pump, and a sensor. The harvest pump is connected in series with the filtration system and is configured to pump the liquid media from the bioreactor vessel through the filtration system. The sensor is configured to interact with the liquid media inside the filtration assembly. The controller executes operations. The operations include receiving, from the sensor, information indicative of an operational state of the filtration system. The operations further include determining, based on at least the received information, whether the filtration system is in an operable state. The operations further include, responsive to a determination that the tangential flow is not in an operable state, causing the harvest pump to stop pumping liquid media through the filtration system.

In yet another embodiment of the disclosure, a method is provided. The method includes at least partially filling a bioreactor vessel with cells and liquid media. The bioreactor vessel is in fluid communication with a first filtration system and a second filtration system. The second filtration system is connected in parallel with the first filtration system. The method further includes pumping liquid media from the bioreactor vessel through the first filtration system using a first harvest pump. The first harvest pump is connected in series with the first filtration system. The method also includes pumping liquid media from the bioreactor vessel through the second filtration system using a second harvest pump. The second harvest pump is connected in series with the first filtration system. The method additionally includes receiving, from a sensor configured to interact with the liquid media, information indicative of an operational state of the first filtration system. Further, the method includes determining, based on at least the received information, whether the first filtration system is in an operable state. Still further, the method includes, responsive to a determination that the first filtration system is not in an operable state, causing the first harvest pump to stop pumping liquid media through the first filtration system.

Other aspects, embodiments, and implementations will become apparent from the following detailed description and claims, with reference, where appropriate, to the accompanying drawings.

DETAILED DESCRIPTION

Figure 1:
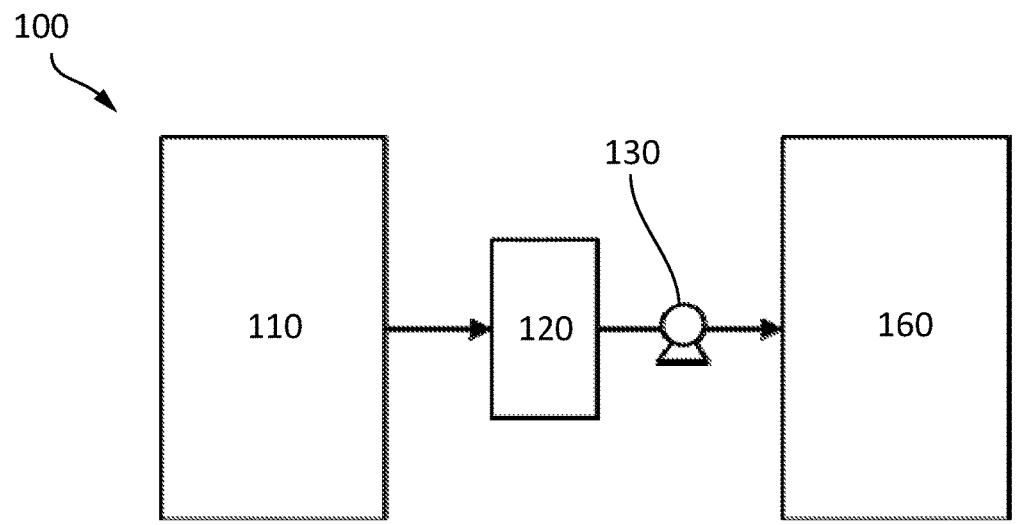
FIG. 1 shows a schematic of a standard perfusion bioreactor setup.

This disclosure generally relates to a filtration system for a cell culture apparatus and a method of cell culture. The perfusion cell culture apparatus of the disclosure comprises a bioreactor vessel and two or more filtration systems (e.g., alternating tangential flow filters) connected in parallel. A failure in either filter may be detected by an in-line sensor, and an automated response system functions to sequester the malfunctioning filter by stopping the flow of liquid media through the filter. Media flow through the remaining operable filters can be increased so that the rate of perfusion through the bioreactor remains relatively unchanged. The cell culture apparatus of the disclosure may prevent issues that arise from filter failures in conventional perfusion bioreactors, thereby improving the long-term viability of cell cultures.

Exemplary methods, devices, and systems are presently disclosed. It should be understood that the terms "example" or "exemplary" are used in the present disclosure to mean "serving as an instance or illustration." Any implementation or feature presently disclosed as being "exemplary" or as being an "example" is not necessarily to be construed as preferred or advantageous over other implementations or features. Other implementations can be utilized, and other changes can be made, without departing from the scope of the subject matter presented in the present disclosure.

Thus, the exemplary implementations presently disclosed are not meant to be limiting. Components presently disclosed and illustrated in the figures can be arranged, substituted, combined, separated, and designed in a wide variety of different configurations, which are contemplated in the present disclosure.

Further, unless context suggests otherwise, the features illustrated in each of the figures can be used in combination with one another. Thus, the figures should be generally viewed as components of one or more overall implementations, with the understanding that not all illustrated features are necessary for each implementation.

In an effort to provide technical context for the present disclosure, the information in this section can broadly describe various components of the implementations presently disclosed. Unless defined otherwise, all technical and scientific terms used herein have the same meanings as commonly understood by those of ordinary skill in the art. Such information is provided solely for the benefit of the reader and, as such, does not expressly limit the claimed subject matter. Further, components shown in the figures are shown for illustrative purposes only. As such, the illustrations are not to be construed as limiting. As is understood, components can be added, removed, or rearranged without departing from the scope of this disclosure.

I. Overview

For particular applications, it may be advantageous to provide a cell culture apparatus that automatically detects and responds to a filtration system failure. Such a cell culture apparatus could include built-in redundancy, such that a second and/or further filtration system can be used if and when a first filter fails (e.g., by rupturing, clogging, fouling, or some other means). Upon filter failure, an automated response system may function to stop media flow to the affected filter, while increasing throughput through any remaining filters. This response may allow perfusion of liquid media to continue at approximately the same rate, without the need for immediate intervention by an operator of the cell culture apparatus. Such a system may improve cell viability and reduce the chance of failure in perfusion bioreactor systems.

The apparatus and methods of the present disclosure generally relate to a perfusion cell culture apparatus with an improved tangential flow filtration system. The apparatus may include a bioreactor vessel configured to house a cell population and liquid growth media. Fresh liquid media may be provided to the bioreactor vessel, and spent liquid media may be removed at an approximately equal rate through a series of filtration assemblies. Each filtration assembly may include a filtration system, a harvest pump, a sensor, and/or a guard filter.

During normal operation, spent liquid media is removed through one or more of the filtration assemblies and pumped into a downstream capture operation. Sensors provided in each filtration assembly may continuously monitor the operation of the filtration assemblies, and determine when a malfunction (e.g., a rupture, a clog, or some other failure mode) occurs in one of the filtration systems.

When a malfunction is detected by one or more of the sensors, an automated response system acts to change the operating parameters of the apparatus so that perfusion of liquid media continues without interruption. The automated response system is carried out by a controller in communication with a sensor and harvest pump. Responsive to determining that one or more of the filtration systems is not in an operable state, the controller may cause a harvest pump associated with the inoperable filter to cease pumping liquid media to the affected filter. Additionally, the controller may cause the remaining operable filtration assembly to process an increased amount of liquid media, e.g., by causing the associated harvest pump to increase liquid media flow to the operable filtration system. The controller may also cause the apparatus to output a notification, for instance, an alarm, an indicator light, or some other alert. The controller may also shut down the filtration system (e.g., by causing a tangential flow pump of the filtration system to stop pumping liquid media across a filter membrane.) In some scenarios, the controller may also stop a downstream capture operation or actuate vales to stop liquid media flow and/or divert liquid media to a waste container. In still another scenario, the controller may completely shut down flows in and out of the bioreactor vessel if a bioreactor sensor (e.g., capacitance, optical density, oxygen uptake rate, etc.) drops below a certain threshold. Other automated responses are also contemplated.

II. Cell Culture Apparatus

Figure 2:
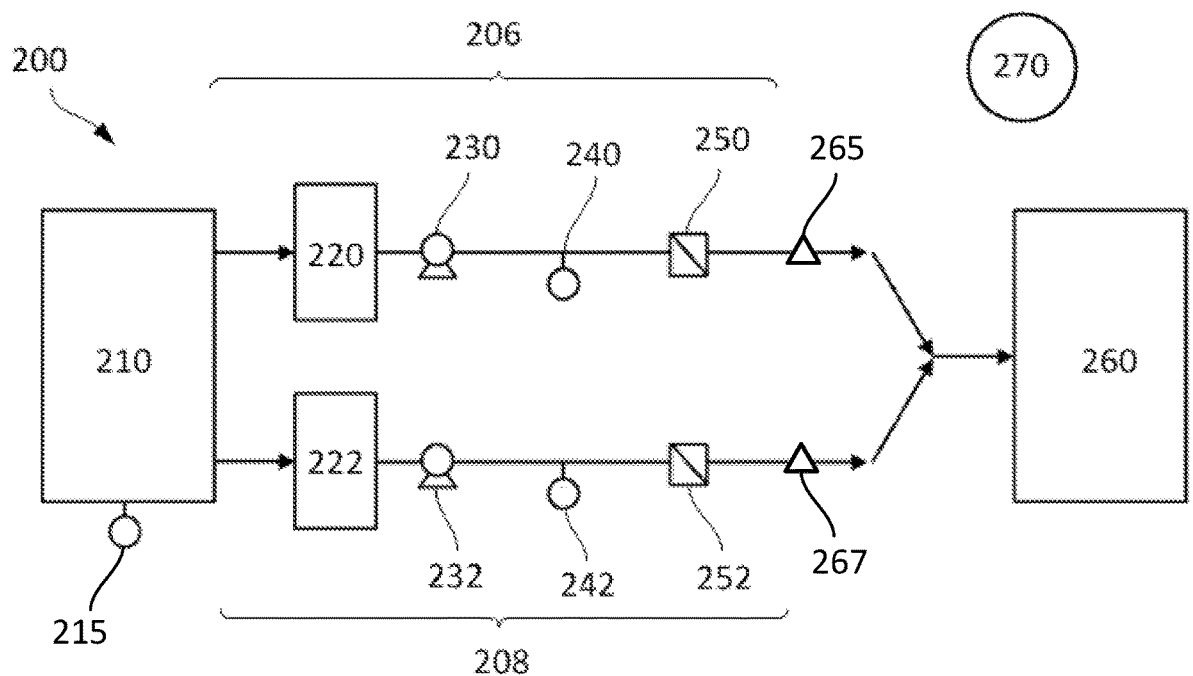
FIG. 2 shows a schematic of a perfusion cell culture apparatus with dual filtration systems and integrated capture according to one embodiment of the disclosure.

A cell culture apparatus according to one embodiment of the present disclosure is illustrated in FIG. 2. The cell culture apparatus 200 includes a bioreactor vessel 210, a continuous capture operation 260, and at least a first filtration assembly 206 and second filtration assembly 208 connected in parallel between at least one outlet of the bioreactor vessel 210 and an inlet of the continuous capture operation 260. The bioreactor vessel 210 of the cell culture apparatus 200 is configured to receive fresh liquid media in order to maintain the cell population within the vessel. As used herein, liquid media may refer to a nutritional growth medium or culture medium designed to support the growth of cells. An approximately equal flow of spent liquid media is pumped out of the bioreactor vessel 210 through the plurality of filtration assemblies 206, 208, thereby removing metabolic and protein waste materials while maintaining a constant volume of media within the bioreactor vessel 210. In order to monitor the environment of the cell culture, a bioreactor sensor 215 may be positioned so that it interacts with liquid media inside the bioreactor vessel 210. Such a bioreactor sensor 215 could be configured to measure a temperature, dissolved oxygen, pH, $pCO_2$, and/or cell density of the bioreactor vessel 210 and/or liquid media inside the bioreactor vessel 210.

The cell culture apparatus 200 may be integrated with a continuously operating capture operation 260 that is configured to collect product (e.g., a desired biologic or therapeutic product) from the liquid media. The capture operation 260 is in fluid communication with the bioreactor vessel 210 by way of at least the first filtration assembly 206. The capture operation 260 may receive spent liquid media after it passes through the parallel filtration assemblies 206, 208 and process and/or purify the media to harvest a desired product of interest. In various embodiments, the capture operation 260 could employ a variety of techniques to harvest the product of interest. For instance, in some examples the capture operation 260 could include a continuous chromatography system including one or more chromatography columns. In particular examples, the capture operations 260 could include a periodic continuous counter-chromatography (PCC) skid, or a simulated moving bed (SMB) skid. In other examples, the capture operation 260 could include a multi-chromatography (MCC) skid (i.e., a continuous chromatography system including multiple columns). Other purification methods may be envisioned by one of ordinary skill in the art.

Before reaching the continuous capture operation 260, the liquid media is flowed through one or more filtration assemblies 206, 208 designed to retain cells in the bioreactor vessel 210. Each filtration assembly 206, 208 is in fluid communication with the bioreactor vessel 210 and may be connected to an outlet of the vessel 210 in between the vessel 210 and the continuous capture operation 260. As shown in FIG. 2, in some examples two filtration assemblies may be connected in parallel to provide two parallel fluid pathways. A first filtration assembly 206 includes a first filtration system 220, a first harvest pump 230, a first sensor 240, and a first guard filter 250. Similarly, a second filtration assembly 208 includes a second filtration system 222, a second harvest pump 232, a second sensor 242, and a second guard filter 252. The elements of each filtration assembly 206, 208 may be connected in series via one or more conduits, sterile tubing, or another connection means. As shown in FIG. 2, the first harvest pump 232 may be connected downstream of the first filtration system 220, and the sensor 240 may be located downstream of the first harvest pump 230, disposed between the first harvest pump 230 and a guard filter 250 connected yet further downstream. In this context, "downstream" refers to a relative location or orientation of an element relative to the flow of liquid media through the filtration assemblies 206, 208, where "downstream" refers generally to the direction toward the capture operation 260 and away from the bioreactor vessel 210. However, elements of the first filtration assembly 206 may be connected in any number of configurations. A second filtration assembly 208 and/or further filtration assembly may be arranged with elements in substantially the same configuration as the first filtration assembly 206, or in a different configuration entirely.

In some examples, a second filtration assembly 208 is configured to operate in parallel (i.e., simultaneously) with the first filtration assembly 206. During normal operation of the cell culture apparatus 200, the flow rate of liquid media through the first filtration assembly 206 and second filtration assembly 208 could be approximately equal. In other words, each filtration assembly 206, 208 may receive an approximately equal flow rate of spent liquid media from the bioreactor vessel 210. However, in other embodiments, a single filtration assembly (e.g., the first filtration assembly 206) may operate at a time, and second filtration assembly 208 and/or further filtration assembly may operate as backup.

In some examples, a third or further filtration assembly may be connected in parallel with the first filtration assembly 206 and second filtration assembly 208 in order to increase throughput, provide an additional backup filtration means in case of a system failure, or provide some other benefit.

The first filtration assembly 206 and the second filtration assembly 208 include a first filtration system 240 and a second filtration system 242, respectively. The first and second filtration systems 220, 222 may be configured to prevent cells in the bioreactor vessel 210 from entering the continuous capture operation 260, while allowing the free passage of cellular wastes and one or more desired products of interest. As used herein, the term "filtration system" is used to refer to a filter-based means for retaining cells within the bioreactor vessel 210. In some examples, the first filtration system 220 and the second filtration system 222 could include filters that function by flowing a fluid (e.g., the liquid media) tangentially across a filter membrane. Such a filtration system 220, 222 could include conventional tangential flow filtration (TFF) systems, cross-flow filters, and similar cell retention means. In another example, at least one of the first filtration system 220 and the second filtration system 222 include alternating tangential flow (ATF) filters. Such filters typically include a filter membrane and a tangential flow pump (e.g., a diaphragm pump) configured to direct fluid tangentially across the filter membrane. The tangential flow pump may include a diaphragm that is actuated to flow liquid media from the bioreactor vessel 210 across the surface of the filter membrane in a repeated back and forth pattern. The repeated perturbation of fluid near the filter membrane may prevent the buildup of cells and minimize fouling of the filter surface during operation. In some examples, a first tangential flow pump provided by the first filtration system may be operated independently from a second tangential flow pump provided by the second filtration system. However, in other embodiments the two or more tangential flow pumps may be controlled in a unified way, such that their pumping action is entirely synchronized or anti-synchronized.

While the first filtration assembly 206 and the second filtration assembly 208 have insofar been described as including ATFs or other tangential flow-based filters, other filtration means may be implemented to retain cells in the bioreactor vessel 210. For example, in other embodiments, the first filtration system 220 and the second filtration system 222 could include internal spin filters (ISF), hollow fiber filters, porous membrane filters, depth filters, and/or other microfiltration or ultrafiltration systems.

The first filtration system 220 and the second filtration system 222 include a first filter membrane and a second filter membrane, respectively. The pore size of the filter membranes may be selected such that a desired product of interest, cellular waste, and spent liquid media are free to flow through the membrane, while cells are retained within the bioreactor vessel 210. The filter membrane of filtration systems 220, 222 may be made up of any material with a suitable pore size, for instance, a porous polymeric membrane. In some examples, the filter membrane is comprised of a series of selectively permeable hollow fibers organized in a parallel array inside of a housing or cartridge. The pore size of the hollow fiber membrane may be selected to achieve the desired permeability of the filtration systems 220, 222. In some examples, each of the first filtration system 220 and the second filtration system 222 include a pore size ranging from about 500 kiloDaltons to about 10 microns, or more preferably between about 0.1 micron and about 1 micron.

Each filtration assembly 206, 208 according to the apparatus of the disclosure includes a harvest pump 230. The first filtration assembly 206 includes a first harvest pump 230 connected in series with the first filtration system 220. Similarly, the second filtration assembly 208 includes a second harvest pump 232 connected in series with the second filtration system 222. The first harvest pump 230 and second harvest pump 232 are configured to pump liquid media from the bioreactor vessel 210 through the first filtration system 220 and the second filtration system 222, respectively, and into the downstream capture operation 260. In various examples, the first harvest pump 230 and/or the second harvest pump 232 could include peristaltic pumps, bearingless pumps, diaphragm pumps, or centrifugal pumps. However, other pumps may be used which maintain sterility of the liquid media while pulling the media through the filtration assemblies 206, 208.

The first harvest pump 230 pumps liquid media from the bioreactor vessel 210 through the first filtration system 220 at a first flow rate. The second harvest pump 232 likewise pumps liquid media from the bioreactor vessel 210 through the second filtration system 222 at a second flow rate. In some examples, the first flow rate could be approximately equal to the second flow rate. In other words, the first harvest pump 230 and the second harvest pump 232 may be configured to pump an approximately equal amount of liquid media through their respective filtration systems 220, 222, such that the filtration assemblies process an equal amount of spent liquid media under normal operating conditions. However, in another embodiment, the first flow rate and the second flow rate may be different. In a particular example, the first harvest pump 230 may operate alone and independently, while the second harvest pump 232 (i.e., a second or further harvest pump connected to a second or further filtration apparatus) may be configured to operate responsive to a determination that the first harvest pump 230, the first filtration system 220, and/or the first filtration assembly 206 is not in an operable state.

The flow rate of liquid media through the filtration assemblies 206, 208 may be approximately equal to a flow rate of fresh media into the bioreactor vessel 210 such that a steady amount of liquid media is maintained in the vessel 210 during perfusion. In other words, the sum of the first flow rate and the second flow rate could be approximately equal to a flow rate of liquid media into the bioreactor vessel 210 (i.e., the flow rate of media introduced to the vessel 210 by a feed operation).

The flow rate of liquid media through each filtration system 220, 222 (i.e., the first flow rate and the second flow rate) may be controlled independently by a controller 270 in communication with the first harvest pump 230 and the second harvest pump 232. The controller 270 may be configured to cause the first harvest pump 230 and/or second harvest pump 232 to increase, decrease, or stop the flow of liquid media through the first filtration system 240 and/or second filtration system 242 depending on the operating conditions of the apparatus 200. For instance, upon failure of one or more of the filtration systems 220, 222, the harvest pump of the affected assembly may be turned off, while the flow rate of liquid media through a remaining filtration assembly could be increased to compensate for the malfunctioning filtration assembly.

While perfusion bioreactor systems are typically configured to run for an extended period of time, equipment failures may be anticipated. In particular, filtration systems 220, 222 may be prone to malfunction, potentially leading to problems in the downstream capture operation 260, increased impurities in the harvest, and in some cases an entire run shutdown. To prevent cells that breach the filtration system(s) 220, 222 from interfering with a continuous capture operation 260, a guard filter 250, 252 may be connected in series with the first filtration system 220 and/or second filtration system 222. Such a guard filter 250, 252 could be configured to prevent cells and cell debris from passing downstream to the capture operation 260, while freely allowing the diffusion of nutrients, metabolic products, and liquid media. As illustrated in FIG. 2, a guard filter 250 could be connected in series with the first filtration system 220 and/or the first filtration assembly 206. In some examples, the guard filter 250 is connected downstream of the first filtration system 220 and/or the sensor 240. The second filtration assembly 208 may also include a guard filter (i.e., a second guard filter 252) connected in series with the second filtration system 222 downstream of the filtration system 222. However, in other embodiments (and as pictured in FIG. 3), multiple filtration assemblies may converge on a single shared guard filter located e.g., at an inlet of the continuous capture operation 260. Other locations and configurations of a guard filter 250 are envisioned.

Guard filters 250, 252 may be made up of any material with suitable porosity, for instance, a porous polymer membrane and/or a hollow fiber membrane. In some cases, the guard filter 250 includes a pore size of about 500 kiloDaltons to about 10 microns, or more preferably from about 0.1 micron to about 1 micron. The guard filter 250 may be configured with a pore size that is approximately equal to the pore size of the first filtration system 220 and/or second filtration system 222 (i.e., so as to mimic the selective permeability of filtration systems 220, 222). However, in other cases the guard filter 250 could comprise a smaller or larger pore size than the filtration systems 220, 222, thereby allowing for the selective filtering of additional metabolic products.

In some cases, at least one sensor 240 may be provided within a filtration assembly 206, 208 to monitor operation of the one or more filtration systems 220, 222 and/or detect a filter failure. In particular, the first filtration assembly 206 may include a sensor 240. In some examples, the second filtration assembly 208 may include a further sensor (e.g., second sensor 242). The sensor 240 could be positioned along a conduit of a filtration assembly 206, 208 and could be configured to interact with the liquid media in the filtration assembly 206, 208, i.e., so as to detect various aspects of the liquid media passing through the filtration assembly 206, 208. As shown in FIG. 2, a sensor 240 could be disposed downstream of the first filtration system 220 and upstream of the guard filter 250. In some cases, the sensor 240 could include a pressure sensor, or, more particularly, a piezoresistive pressure sensor. The sensor 240 could be configured to detect a pressure in the first filtration assembly 206 (e.g., a pressure of the liquid media inside the first filtration assembly 206), which may be indicative of a clogged guard filter 250 and/or a rupture in the upstream first filtration system 220. In various examples, the sensor 240 could be configured to detect a pressure upstream or downstream of the first guard filter 250, a pressure upstream or downstream of the first filtration system 220, and/or a transmembrane pressure across the first filtration system 220 or guard filter 250. In other examples, the sensor 240 could be an optical sensor (e.g., an optical density probe), and the sensor 240 could be configured to determine a cell density in the liquid media flowing through the first filtration assembly 206. In further examples, the sensor 240 could include a flow meter operable to measure a flow rate of liquid media through the filtration systems 220, 222 and/or filtration assemblies 206, 208. In yet further examples, the sensor 240 may include a capacitance sensor, a Raman sensor, or an FTIR (Fourier transform infrared) sensor. In another example, the sensor 240 could be integrated into the continuous capture operations (e.g., as a pressure sensor upstream of the capture column). Other sensor types and applications are envisioned.

While the sensors 240, 242 in FIG. 2 are illustrated as being included in the first filtration assembly 206 and second filtration assembly 208 (i.e., disposed in a conduit between the filtration systems 220, 222 and the guard filters 250, 252), sensors could be disposed in a variety of locations. For instance, in some examples a bioreactor sensor 215 could be configured to interact with liquid media in the bioreactor vessel 210, such that the bioreactor sensor 215 can monitor changes in pressure, temperature, pH, dissolved oxygen, $pCO_2$, cell density, or other characteristics of the liquid media inside the vessel 210.

To mitigate potential problems stemming from a filter failure, the cell culture apparatus 200 could include an automated response system. The response system may be used to detect a filtration system failure (e.g., a rupture of the filter membrane), sequester the malfunctioning filtration system, and/or adjust operating parameters of the apparatus 200 in order to continue cell perfusion relatively unchanged. The automated response system may be implemented by a controller 270 in communication with at least the harvest pumps 230, 232 and the sensors 240, 242. As described herein, the controller 270 could include at least one processor configured to execute operations (e.g., operations stored as program instructions in a data storage of the controller). However, in other examples the controller 270 could include a comparator or another simplified control system.

The controller 270 may be configured to receive, from the sensors 240, 242, information indicative of an operational state of the first filtration system 220 and/or second filtration system 222. Such information could include characteristics of the liquid media flowing through the first filtration assembly 206 and/or second filtration assembly 208. For instance, the information could include a fluid pressure of the liquid media inside the filtration assemblies 206, 208, a cell density of the liquid media, a flow rate of the liquid media, the presence of an analyte in the liquid media, or some other information. In other examples, as described previously, a bioreactor sensor 215 could be configured to collect information relating to liquid media inside the bioreactor vessel 210, for example, a cell density or another characteristic.

The controller 270 may then determine whether the first filtration system 220 and/or the second filtration system 222 is in an operable state based on at least the received information from the sensor(s) 240, 242. In this context, the term "operable" is used to refer to a filtration system that is functioning as intended, i.e., to selectively pass liquid media containing cellular waste and a product of interest, while retaining the cells within the bioreactor vessel 210. Conversely, a filtration system 220, 222 that is not in an operable state may fail to pass a desired or expected flow rate of liquid media (i.e., indicating a clogged or fouled filter membrane), or fail to retain cells (i.e., indicating the filter has ruptured). Determining whether the filtration system 220, 222 is in an operable state could include determining whether the received information falls within an expected range of values, or falls above or below a predetermined threshold value.

In a particular example, the first filtration system 220 may have ruptured, thereby allowing cells to breach the first filtration system 220 and collect on the guard filter 250. The controller 270 may then receive information from the sensor 240 indicating an increased pressure in the liquid media caused by cells clogging the guard filter 250. Determining whether the first filtration system 220 is in an operable state could then include determining whether a pressure in the first filtration assembly 206 (i.e., a pressure of liquid media inside the first filtration assembly 206) is greater than a threshold value. In a similar example, one or more of the sensors 240 could include an optical sensor (e.g., an optical density probe) and determining whether the filtration system is in an operable state could include determining that a cell density of the liquid media inside the first filtration assembly 206 is above a threshold level, indicating that cells have breached the first filtration system 220. In still another example, the bioreactor sensor 215 could be an optical sensor, and determining whether the filtration systems 220, 222 are in an operable state could include determining that a cell density of the liquid media inside the bioreactor vessel 210 is under a threshold level.

Other failure modes are also anticipated. For example, the first filtration system 220 may be rendered inoperable due to a failure of a first tangential flow pump and/or fouling of the filter membrane (e.g., in cases where the first filtration system 220 is an ATF or other tangential flow-based filter). In such a situation, cells may build up on the filter membrane, preventing or diminishing the flow of liquid media through the first filtration system 220. In such an example, the sensor 240 could be configured to measure a transmembrane pressure across the first filtration system 220. Determining whether the first filtration system 220 is in an operable state could include determining that the transmembrane pressure across the filtration system 220 is above a threshold value. In a further example, the sensor 240 could include a flow meter and determining whether the first filtration system 220 is in an operable state could include determining that flow of liquid media through the first filtration system 220 (and/or the first filtration assembly 206) is below a threshold level. Other failure modes, sensor parameters, and determinants may be envisioned by one of ordinary skill in the art.

After detecting one or more filtration system failures, the automated response system (i.e., controller 270) may function to sequester the malfunctioning filtration assembly 206, 208 by preventing liquid media from flowing through the affected filtration system 220, 222. In other words, responsive to a determination that the first filtration system 220 is not in an operable state, the controller 270 may cause the first harvest pump 230 to stop pumping liquid media through the first filtration system 220 by e.g., cutting off power to the harvest pump 230. The controller 270 could further be configured to shut down the first filtration system 220 by causing a tangential flow pump of the filtration system 220 to stop pumping liquid media across the filter membrane (i.e., in cases where the filtration system 220 includes an ATF). In other examples, the controller 270 could be configured to divert the liquid media to a waste collection system by actuating a waste valve connected in series with the first filtration system 220 or the second filtration system 222. In still another scenario, the controller 270 may completely shut down flows in and out of the bioreactor vessel 210 if information from a bioreactor sensor 215 (e.g., a capacitance, optical density, oxygen uptake rate, or other aspect of liquid media inside the bioreactor vessel 210) drops above or below a certain threshold.

Additionally or alternatively, the first filtration assembly 206 could include a first isolation valve 265 or valves connected in series with the first filtration system 220. The first isolation valve 265 could be configured to control the flow of liquid media through the first filtration system 220. Responsive to a determination that the first filtration system 220 is not in an operable state, the controller 270 could be operable to close the first isolation valve 265. A second isolation valve 267 may further be connected in series with the second filtration system 222 and configured to control the flow of liquid media through the second filtration system 222. As shown in FIG. 2, in some cases the isolation valve(s) 265, 267 could be connected in series between the first filtration assembly 206 and/or the second filtration assembly 208 and the continuous capture operation 260. However, such an isolation valve or valves 265, 267 could be located anywhere before, after, or within the first filtration assembly 206 or the second filtration assembly 208. For example, the first isolation valve 265 and/or second isolation valve 267 could be positioned between the bioreactor vessel 210 and a respective filtration assembly 206 208, located downstream of the filtration system(s) 220, 222, located downstream of the guard filter(s) 250, 252, or connected to an inlet of the continuous capture operation 260. Upon detecting a filter malfunction, the isolation valve(s) 265, 267 may be actuated to prevent flow of liquid media and cellular products through the affected filtration system 220, 222, thereby preventing cells and contaminants from reaching the continuous capture operation 260 and facilitating replacement of any compromised equipment.

In addition to sequestering the broken filtration system 220, 222, the controller 270 could also be operable to change various operating parameters of the cell culture apparatus 200 following a filter failure. As described earlier, a steady flow rate of liquid media should be supplied to the bioreactor vessel 210 and an approximately equal flow rate of waste-containing spent media may be continuously removed to promote the proliferation of cells within the bioreactor vessel 210. Following detection of a failure in the first filtration system 220, the controller 270 may be additionally configured to increase a flow rate of liquid media through a remaining operable second filtration system 222 such that a steady perfusion of liquid media is maintained in the bioreactor vessel 210. The increased flow rate through the remaining operable filtration system (e.g., the second filtration system 222) should be approximately equal to the total pre-failure flow rate through the original filtration system(s) 220, 222 (e.g., the sum of the first flow rate through the first filtration system 220 and the second flow rate through the second filtration system 222). In one example, the controller 240 could be operable to cause the second harvest pump 232 to increase a flow rate of liquid media through the second filtration system 242 responsive to a determination that the first filtration system 220 is not in an operable state. In some examples, causing the second harvest pump 232 to increase the flow of liquid media through the second filtration system 242 could include approximately doubling the flow rate.

In some cases, the cell culture apparatus 200 could include a plurality of filtration assemblies (i.e., at least a first filtration assembly 206 and a second filtration assembly 208) connected in parallel and operating simultaneously. For example, in some embodiments the cell culture apparatus 200 may include three, four, six, or more filtration assemblies in order to achieve a desired perfusion rate. Upon failure of one or more of the filtration systems 220, 222 of the filtration assemblies 206, 208, the controller 270 may be operable to adjust the flow rate through any number of remaining operable filter assemblies to maintain steady perfusion of liquid media in the system. For example, responsive to determining that a first filtration system 220 is not in an operable state, the controller 270 may cause one or more harvest pumps associated with one or more further filtration assemblies to increase a flow rate of liquid media through their respective filtration systems.

In some examples, it may be desirable to notify an operator of the cell culture apparatus 200 when a filter malfunction has been detected. For instance, responsive to a determination that the first filtration system 220 is not in an operable state, the controller 270 may be configured to output a notification. Such a notification could include a visual alert, for example, a blinking light, a colored light, a visual message, textual or graphical information on a display. Additionally or alternatively, the notification could include an auditory alert, such as an alarm sound, a beeping, a ringing, an auditory message, or some other auditory component. In still another example, the notification could include a text message, a phone call, or an e-mail sent to a recipient associated with the cell culture apparatus.

Figure 3:
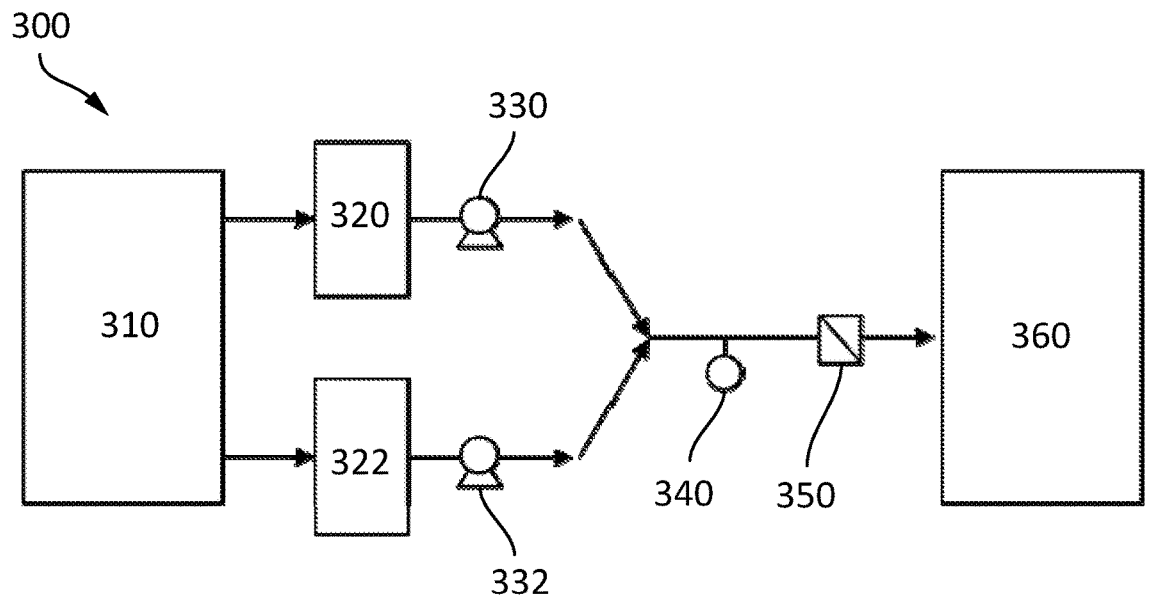
FIG. 3 shows a schematic of a perfusion cell culture apparatus with dual filtration systems and integrated capture according to another embodiment of the disclosure.

While the cell culture apparatus 200 pictured in FIG. 2 includes two filtration assemblies 206, 208 including separate filtration systems 220, 222, sensor(s) 240, 242, and guard filters 250, 252, simpler cell culture apparatuses may fit within the scope of this disclosure. For instance, FIG. 3 illustrates a cell culture apparatus 300 including dual filtration systems 320, 322 that converge on a shared sensor 340, guard filter 350, and capture operation 360. The first filtration system 320 is connected in series with a first harvest pump 330, while the second filtration system 322 is connected in series with a second harvest pump 332. Such a configuration may allow for detection of an overall failure of the cell culture apparatus 300 by way of the sensor 350. For example, when a rupture in either the first filtration system 320 or the second filtration system 322, cells from the bioreactor vessel 310 may quickly flow through the filtration systems 320, 322 and collect on the guard filter 350. A clog in the guard filter 350 may cause a pressure increase in the liquid media upstream of the guard filter 350, which could be detected by a pressure sensor (e.g., sensor 340). However, owing to the shared downstream sensor 340, such a system may be unable to discern between a failure in the first filtration system 320 and a failure in the second filtration system 322. In such an example system, an automated response system could function to e.g., alert an operator of the cell culture apparatus 300 by outputting a notification, divert the liquid media to a waste collection system, or stop the continuous capture operation. Other automated responses are contemplated.

The bioreactor vessel 310, first and second filtration systems 320, 322, first and second harvest pumps 330, 332, sensor 340, guard filter 350, and capture operation 360 shown in FIG. 3 may be similarly configured to the corresponding components described above in relation to FIG. 2.

Figure 4:
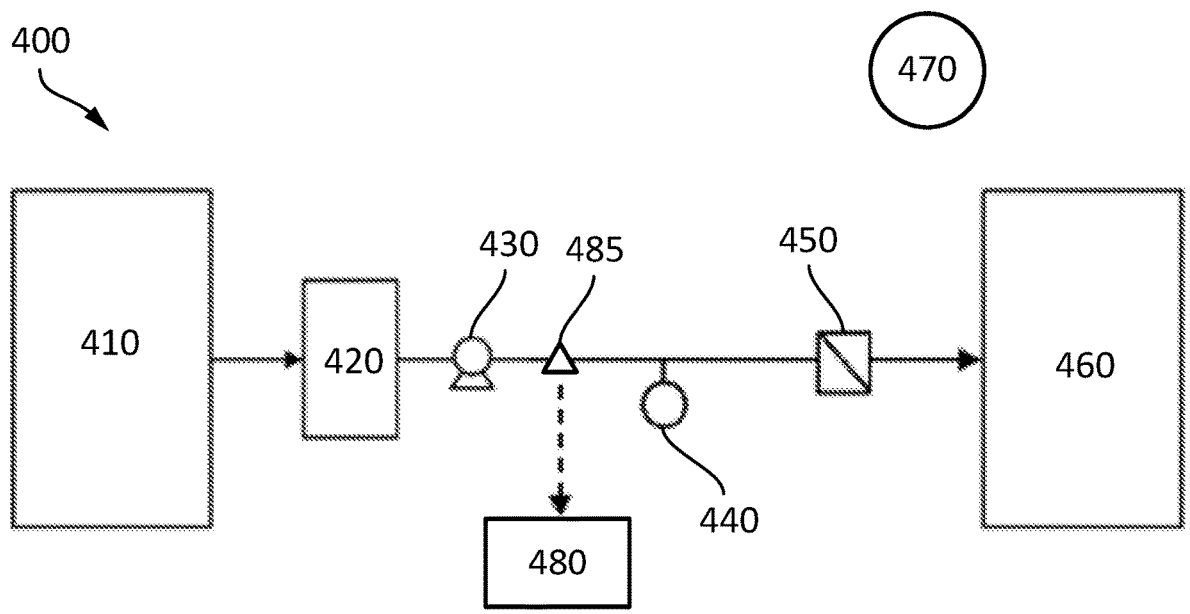
FIG. 4 shows a schematic of a perfusion cell culture apparatus setup with a single filtration system according to another embodiment of the disclosure.

In some other examples a cell culture apparatus may rely on a single filtration assembly for processing spent liquid media. FIG. 4 illustrates an example of such a cell culture apparatus 400. Here, a bioreactor vessel 410 is in fluid communication with a capture operation 460 by way of a single filtration system 420, harvest pump 430, sensor 440, and guard filter 450. A controller 470 may be communicatively coupled to at least the sensor 440 and the harvest pump 430. In such an example, a filter malfunction (e.g., a rupture, a clog, or another defect of the filtration system 420) could render the entire filtration mechanism of the cell culture apparatus 400 inoperable. Responsive to a determination that the filtration system 420 is not in an operable state, the controller 470 could be operable to cause the capture operation 460 to stop collecting product from the liquid media.

In situations where all filtration assemblies of a cell culture apparatus are inoperable (e.g., when a singular filtration system 420 fails, or when all of a plurality of filtration systems fail), it may be advantageous to divert the flow of liquid media to a waste collection system 480. To provide for such a scenario, one or more filtration assembly could include a waste valve 485 connected in series with the filtration system 420. The waste valve 485 may be configured to divert the flow of liquid media to a waste collection system 480. The waste valve 485 could be a three-way valve, however in other examples the waste valve 485 could include one or more two-way valves. Such a waste valve 485 may preferably be connected downstream of the harvest pump 430 and upstream of the guard filter 450, however a variety of locations could be envisioned. Responsive to a determination that the filtration system 420 is not in an operable state, the controller 470 could be configured to open the waste valve 485, thereby diverting the liquid media to waste.

Diverting liquid media into a waste collection system 480 may allow for temporary continuation of perfusion through the cell culture system 400. However, eventually the cell density in the bioreactor vessel 410 may drop to an unacceptable level as more cells are pumped into waste. To prevent an undesired amount of cell density loss, a sensor (e.g., sensor 440 or a further bioreactor sensor) may be configured to interact with liquid media inside the bioreactor vessel 410 and/or monitor cell density in the vessel 410. Responsive to a determination that cell density falls below a threshold value, the controller 470 could be configured to stop perfusion altogether by e.g., closing the waste valve 485, closing an isolation valve, causing one or more harvest pumps 420 to stop pumping liquid media through one or more filtration systems 420, or by some other means.

The bioreactor vessel 410, filtration system 420, harvest pump 430, sensor 440, guard filter 450, capture operation 460, and controller 470 shown in FIG. 4 may be similarly configured to the corresponding components described above in relation to FIG. 2.

III. Cell Culture Method

Figure 5:
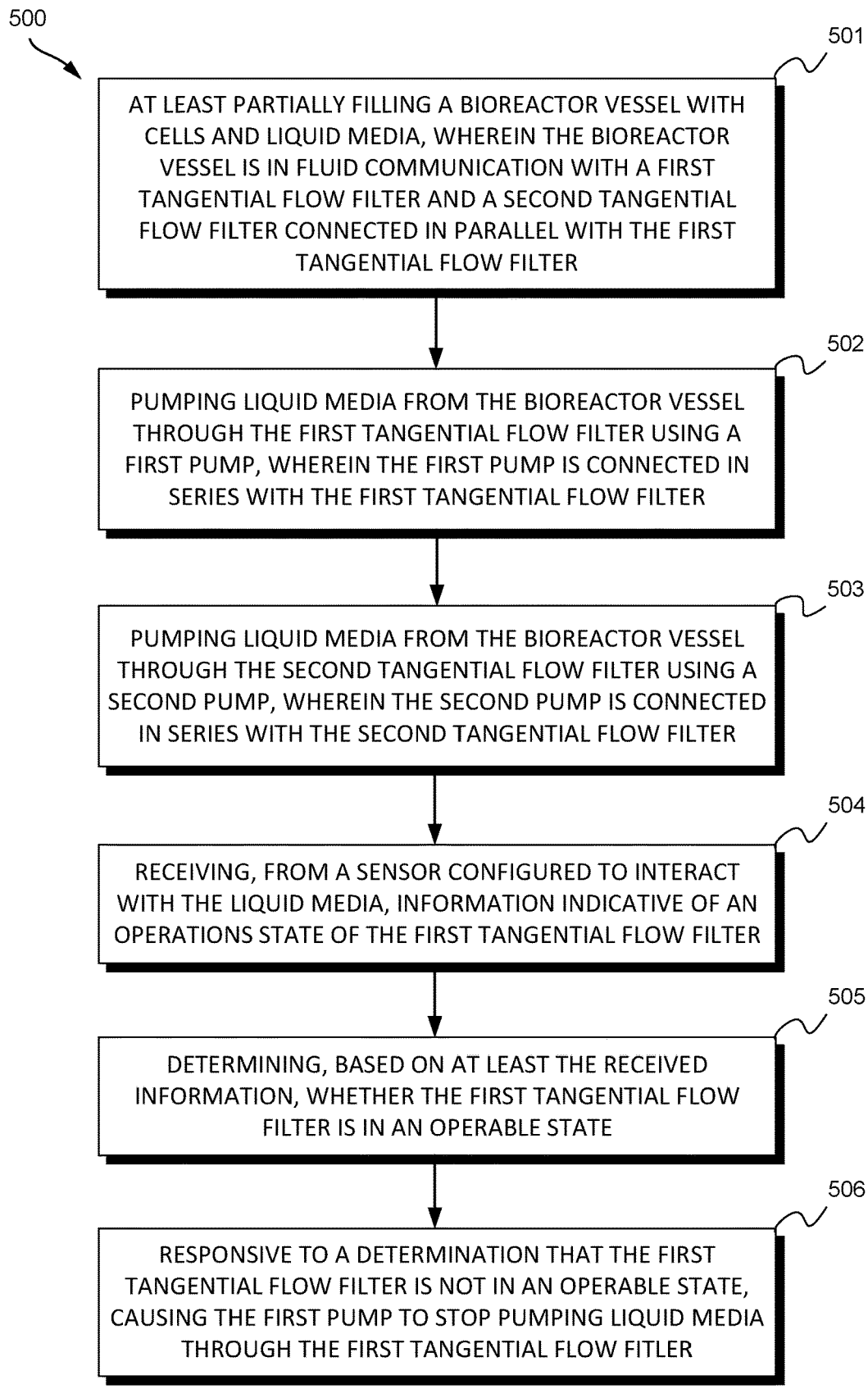
FIG. 5 shows a flowchart of a method according to an embodiment of the disclosure.

FIG. 5 is a flowchart of a method 500 for operating a cell culture apparatus, such as any of the apparatuses shown in FIG. 2, 3, or 4 and described herein. For purposes of illustration, the cell culture apparatus operated in method 500 includes: (i) a bioreactor vessel; (ii) a first filtration system in fluid communication with the bioreactor vessel; (ii) a second filtration system in fluid communication with the bioreactor vessel; (iii) a first harvest pump connected in series with the first filtration system; (iv) a second harvest pump connected in series with the second filtration system; and (v) a sensor configured to interact with liquid media flowed through at least the first filtration system.

Block 501 of method 500 includes at least partially filling a bioreactor vessel with cells and liquid media. The bioreactor vessel is in fluid communication with a first filtration system and a second filtration system connected in parallel with the first filtration system. At least partially filling a bioreactor vessel with cells and liquid media could include providing cells as a monolayer on an artificial substrate (i.e., an adherent culture) In other examples, at least partially filling a bioreactor vessel with cells and liquid media could include providing cells free-floating in the media (i.e., as a suspension culture). Liquid media for continuous perfusion may be provided by a feed operation configured to continuously introduce fresh liquid media into the bioreactor vessel. Liquid media from the feed operation may be provided at a predetermined flow rate tailored to the nutritional needs of the cells within the bioreactor vessel.

Block 502 of method 500 includes pumping liquid media from the bioreactor vessel through the first filtration system using a first harvest pump. Block 503 of method 500 includes pumping liquid media from the bioreactor vessel through the second filtration system using a second harvest pump. The first harvest pump could be connected in series with the first tangential flow. Likewise, the second harvest pump may be connected in series with the second filtration system.

Pumping liquid media through the first filtration system could include pumping liquid media at a first flow rate. Pumping liquid media through the second tangential flow rate could include pumping liquid media at a second flow rate. In some examples, the first flow rate may be substantially equal to the second flow rate under normal operating conditions. However, in other examples, the flow rate of liquid media through the first filtration system may be different than the flow rate of liquid media through the second filtration system. Additionally or alternatively, the sum of the first flow rate and the second flow rate could be approximately equal to a flow rate of media into the bioreactor vessel by a feed operation (e.g., the feed operation described previously in relation to block 501 of method 500).

Block 504 of method 500 includes receiving, from a sensor configured to interact with liquid media flowed through at least the first filtration system, information indicative of an operational state of the first filtration system. Such a sensor may be located within a filtration assembly that includes the first filtration system, the first harvest pump and/or other elements. Additionally or alternatively, the sensor could be disposed within a conduit connected in series with the first filtration system and/or the first harvest pump.

In some examples, the sensor is a pressure sensor (e.g., a piezoresistive pressure sensor). Information indicative of an operational state of the first filtration system could include information relating to a pressure in liquid media flowing through the first filtration system. More specifically, the information could include a pressure in the liquid media upstream of the first filtration system, a pressure in the liquid media downstream of the first filtration system, or a differential transmembrane pressure in the liquid media across the first filtration system. In some examples, the cell culture apparatus includes a guard filter connected in series with the first filtration system downstream of the first filtration system. In such an example, the information could include a pressure in the liquid media upstream of the guard filter. Additionally or alternatively, the sensor could include a capacitance sensor, a Raman probe, an FTIR probe, or an optical density probe. In such examples, the information could include information relating to a cell density of cells in the liquid media (e.g., the liquid media downstream of the first filtration system).

Block 505 of method 500 includes determining, based on at least the received information, whether the first filtration system is in an operable state. When first filtration system is not in an operable state, the filter may pass a desired or expected flow rate of liquid media (i.e., indicating a clogged or fouled filter membrane), or fail to retain cells (i.e., indicating the filter has ruptured). Determining whether the filtration system is in an operable state could include determining whether the information received from the sensor falls within an expected range of values, or falls above or below a predetermined threshold value. In some examples, the sensor is a pressure sensor, and determining whether the first filtration system is in an operable state includes determining that a pressure of the liquid media is above a predetermined threshold value. In some cases, determining whether the first filtration system is in an operable state could include determining that a transmembrane pressure across the first filtration system is above a predetermined threshold value. In still further examples, determining whether the first filtration system is in an operable state could include determining that a cell density of the liquid media (e.g., the liquid media in the bioreactor vessel, or liquid media flowing through the first filtration system) is outside of a predetermined threshold range.

Block 506 of method 500 includes, responsive to a determination that the first filtration system is not in an operable state, causing the first harvest pump to stop pumping liquid media through the first filtration system. Such a response may effectively stop the flow of liquid media through the first filtration system. Additionally or alternatively, an isolation valve may be connected in series with the first filtration system and configured to control the flow of liquid media through the first filtration system. In such an example, method 500 could include, responsive to a determination that the first filtration system is not in an operable state, closing the isolation valve. Other responses to a malfunctioning filter are also anticipated.

In some examples, method 500 could further include adjusting a flow rate of one or more remaining operable filters. For example, the method 500 may further include causing the second harvest pump to increase a flow rate of liquid media through the second filtration system responsive to a determination that the first filtration system is not in an operable state. Increasing the flow rate of liquid media through the second filtration system could allow perfusion of liquid media through the bioreactor vessel to continue at steady rate following a filter failure. In other words, the adjusted flow rate of liquid media through the second filtration system may be approximately equal to the flow rate of liquid media through an operable first and second filtration system. In some examples, causing the second harvest pump to increase a flow rate of liquid media through the second filtration system could include approximately doubling the flow rate of liquid media through the second filtration system.

In some examples, method 500 further includes outputting a notification responsive to a determination that the first filtration system is not in an operable state. The notification may comprise a visual alert (e.g., a blinking light, a colored light, a visual message, textual or graphical information on a display) and/or an auditory alert (e.g., an alarm sound, a beeping, a ringing, an auditory message, or some other auditory component). In yet further examples, method 500 could include diverting liquid media to waste collection system, stopping a downstream capture operation, or affecting other aspects of the operation of a cell culture apparatus.

The exemplary method 500 illustrated in FIG. 5 is meant as an illustrative, non-limiting example. Blocks and steps described herein may be carried out sequentially or in parallel. Furthermore, the various block and steps could be carried out in a different order than described herein and some blocks and steps could be omitted, skipped, and/or repeated. Additional or alternative elements of the method and additional or alternative components of the systems are contemplated.

While the apparatus and methods disclosed herein have been described in terms of various embodiments, it is understood that variations and modifications will occur to those skilled in the art. Therefore, it is intended that the appended claims cover all such equivalent variations that come within the scope of the apparatus and methods as claimed. In addition, the section headings used herein are for organizational purposes only and are not to be construed as limiting the subject matter described.

All references cited in this application are expressly incorporated by reference herein.

What is claimed is:

1. A perfusion cell culture apparatus comprising:
   (a) a bioreactor vessel configured to receive liquid media comprising a cell culture;
   (b) a first filtration assembly in fluid communication with the bioreactor vessel, wherein the first filtration assembly comprises:
      (i) a first filtration system;
      (ii) a first harvest pump connected in series with the first filtration system, wherein the first harvest pump is configured to pump the liquid media from the bioreactor vessel through the first filtration system; and
      (iii) a sensor, wherein the sensor is configured to interact with the liquid media inside the first filtration assembly; and
   (c) a second filtration assembly configured to operate in parallel with the first filtration assembly, wherein the second filtration assembly is in fluid communication with the bioreactor vessel, and wherein the second filtration assembly comprises:
      (i) a second filtration system; and
      (ii) a second harvest pump connected in series with the second filtration system, wherein the second harvest pump is configured to pump the liquid media from the bioreactor vessel through the second filtration system; and
   (d) a controller, wherein the controller executes operations comprising:
      (i) receiving, from the sensor, information indicative of an operable state of the first filtration system;
      (ii) determining, based on at least the received information from the sensor, whether the first filtration system is in an operable state; and
      (iii) responsive to a determination that the first filtration system is not in an operable state, causing the first harvest pump to stop pumping liquid media through the first filtration system.

2. The perfusion cell culture apparatus of claim 1, wherein at least one of the first filtration system and the second filtration system comprises an alternating tangential flow filter.

3. The perfusion cell culture apparatus of claim 1, wherein at least one of the first filtration system and the second filtration system comprises a tangential flow filter.

4. The perfusion cell culture apparatus of claim 1, wherein each of the first filtration system and the second filtration system comprise a filter membrane having a pore size of about 0.1 micron to about 1 micron.

5. The perfusion cell culture apparatus of claim 1, wherein the sensor comprises a pressure sensor, and wherein determining that the first filtration system is not in an operable state comprises determining that a pressure in the first filtration assembly is greater than a threshold value.

6. The perfusion cell culture apparatus of claim 1, wherein the sensor comprises a capacitance sensor.

7. The perfusion cell culture apparatus of claim 1, wherein the sensor comprises an optical sensor.

8. The perfusion cell culture apparatus of claim 1, wherein the controller is further configured to:
   responsive to the determination that the first filtration system is not in an operable state, cause the second harvest pump to increase a flow rate of liquid media through the second filtration system.

9. The perfusion cell culture apparatus of claim 8, wherein causing the second harvest pump to increase the flow of liquid media through the second filtration system comprises approximately doubling the flow rate.

10. The perfusion cell culture apparatus of claim 1, wherein the controller is further configured to:
   responsive to the determination that the first filtration system is not in an operable state, output a notification.

11. The perfusion cell culture apparatus of claim 10, wherein the notification comprises a visual alert or an auditory alert.

12. The perfusion cell culture apparatus of claim 1, further comprising an isolation valve connected in series with the first filtration assembly, wherein the valve is configured to control the flow of liquid media through the first filtration assembly, and wherein the controller is further configured to:
   responsive to the determination that the first filtration system is not in an operable state, close the isolation valve.

13. The perfusion cell culture apparatus of claim 1, wherein the first filtration assembly further comprises a guard filter connected in series with the first filtration system, wherein the guard filter is connected downstream of the first filtration system and the sensor.

14. The perfusion cell culture apparatus of claim 13, wherein the guard filter comprises a pore size of about 0.1 micron to about 1 micron.

15. The perfusion cell culture apparatus of claim 1, further comprising a capture operation configured to collect product from the liquid media, wherein the capture operation is in fluid communication with the bioreactor vessel by way of at least the first filtration assembly, wherein the capture operation comprises multi-column chromatography (MCC).

* * * * *